(12) United States Patent
Meudt

(10) Patent No.: US 7,208,614 B2
(45) Date of Patent: Apr. 24, 2007

(54) METHOD FOR PRODUCING, VIA ORGANOMETALLIC COMPOUNDS, ORGANIC INTERMEDIATE PRODUCTS

(75) Inventor: Andreas Meudt, Floersheim-Weilbach (DE)

(73) Assignee: Archimica GmbH, Franfurt am Main (DE)

( * ) Notice: Subject to any disclaimer, the term of this patent is extended or adjusted under 35 U.S.C. 154(b) by 341 days.

(21) Appl. No.: 10/491,966

(22) PCT Filed: Oct. 2, 2002

(86) PCT No.: PCT/EP02/11042

§ 371 (c)(1),
(2), (4) Date: Apr. 8, 2004

(87) PCT Pub. No.: WO03/033503

PCT Pub. Date: Apr. 24, 2003

(65) Prior Publication Data

US 2004/0251563 A1   Dec. 16, 2004

(30) Foreign Application Priority Data

Oct. 12, 2001   (DE) .............................. 101 50 615

(51) Int. Cl.
*C07F 5/02*   (2006.01)
(52) U.S. Cl. .............................. 556/7; 549/206; 549/4
(58) Field of Classification Search .................. 556/7; 549/206, 4
See application file for complete search history.

(56) References Cited

U.S. PATENT DOCUMENTS

| 3,649,701 A | 3/1972 | Smith |
| 6,448,433 B1 * | 9/2002 | Marcuccio et al. ............ 562/7 |
| 2005/0001333 A1 | 1/2005 | Wehle et al. |

FOREIGN PATENT DOCUMENTS

WO   WO 0064905   11/2000

OTHER PUBLICATIONS

Gilman et al., "Secondary & Tertiary Alkyllithium Compounds & Some Interconversion Reactions with Them", J. Amer. Chem. Soc., vol. 63 pp. 2479-2482 (1941).
Bartlett et al. "t-Butyllithium," J. Amer. Chem. Soc. vol. 63 pp. 3229-3230 (1941).
Tarbell et al., "The Action of Lithium on an Optically Active Aliphatic Chloride," J. Amer. Chem. Soc. vol. 61 pp. 1203-120-5 (1939).
Schlosser et al., "Organonetallics in Synthesis, A Manual" John Wiley & Sons, Ltd., pp. 223-347 (2002).
PCT ISR for PCT/EP02/11502, Feb. 6, 2003.
English Translation of PCT IPER for PCT/EP02/11502, Apr. 29, 2004.

* cited by examiner

*Primary Examiner*—Joseph K. McKane
*Assistant Examiner*—Robert Shiao
(74) *Attorney, Agent, or Firm*—ProPat, L.L.C.

(57) ABSTRACT

A method for preparing aryllithium compounds of the formulae (IV) and (VI) includes reacting halogen compounds (I) with lithium metal to obtain a lithium compound of formula (II) and reacting the lithium compound of formula (II) with aromatic compounds of the formulae (III) and/or (V) to form lithium aromatics (IV) and (VI).

12 Claims, No Drawings

METHOD FOR PRODUCING, VIA ORGANOMETALLIC COMPOUNDS, ORGANIC INTERMEDIATE PRODUCTS

This Application is a 311 of PCT/EP02/11042 filed on Oct. 2, 2002.

The invention relates to a process for preparing organic compounds by producing aryllithium compounds and reacting them with suitable electrophiles, in which a lithium compound is firstly generated by reacting halogen compounds with lithium metal and is subsequently reacted with aromatic compounds to deprotonate them and form the desired lithium aromatic which may finally be reacted, if desired, with an appropriate electrophile (equation I), Step 1: Production of the Base

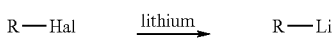

Step 2: Deprotonation of the Substrate

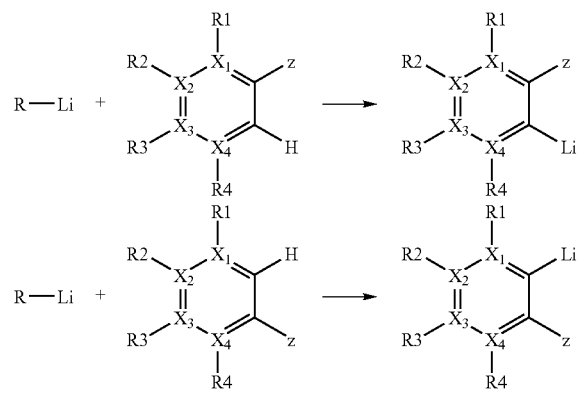

(Equation I)

The upswing in organometallic chemistry, particularly that of the element lithium, in the preparation of compounds for the pharmaceutical and agro-chemical industries and also for numerous further applications has proceeded almost exponentially in recent years if the number of applications or the amount of products produced in this way is plotted against a time axis. Reasons for this are essentially the ever more complex structures of the fine chemicals required for the pharmaceuticals and agrochemicals sectors and also the virtually unlimited synthesis potential of organolithium compounds for the buildup of complex organic structures.

Virtually any organolithium compound can be easily produced by means of the modern arsenal of organometallic chemistry and can be reacted with virtually any electrophile to form the desired product. Most organolithium compounds are generated in one of the following ways:

(1) The most important route without doubt is halogen-metal exchange in which usually bromoaromatics are reacted with n-butyllithium at low temperatures.
(2) Very many organometallic Li compounds can likewise be prepared by reacting bromoaromatics with lithium metal.
(3) Also very important is the deprotonation of organic compounds with lithium alkyls (e.g. BuLi) or lithium amides (e.g. LDA or LiNSi).

It follows from this that the use of commercially available alkyllithium compounds is required for the major part of this chemistry, with n-BuLi usually being used here. The synthesis of n-BuLi and related lithium aliphatics is technically complicated and requires a great deal of know-how, so that n-butyllithium, s-butyllithium, tert-butyllithium and similar molecules are available only at very high prices, judged by industrial standards. This is the most important but by far not the only disadvantage of this otherwise very advantageous and widely usable reagent.

Owing to the extreme sensitivity and, in concentrated solutions, pyrophoric nature of such lithium aliphatics, very elaborate logistic systems for transport, introduction into the metering stock vessel and metering have to be built up, requiring a high capital investment in plant, for the quantities wanted in industrial production (annual production quantities of from 5 to 500 metric tons).

Furthermore, the reactions of n-, s- and tert-butyllithium form either butanes (deprotonations), butyl halides (halogen-metal exchange, 1 equivalent of BuLi) or butene and butane (halogen-metal exchange) which are gaseous at room temperature and are given off in the hydrolytic work-ups of the reaction mixtures which are required. This results in an additional requirement for complicated offgas purification facilities or appropriate incineration facilities in order to meet strict legal pollution regulations. As a way around this problem, specialist companies offer alternatives such as n-hexyllithium, but although these do not result in formation of butanes, they are significantly more expensive than butyllithium.

A further disadvantage is the formation of complex solvent mixtures after the work-up. Owing to the high reactivity of alkyllithium compounds toward ethers which are virtually always solvents for the subsequent reactions, alkyllithium compounds can usually not be marketed in these solvents. Although the manufacturers offer a broad range of alkyllithium compounds of a wide variety of concentrations in a wide variety of hydrocarbons, halogen-metal exchange reactions, for example, do not proceed in pure hydrocarbons, so that one is forced to work in mixtures of ethers and hydrocarbons. As a result, water-containing mixtures of ethers and hydrocarbons are obtained after hydrolysis, and the separation of these is complicated and in many cases cannot be carried out economically at all. However, recycling of the solvents used is an absolute requirement for large-scale industrial production.

For the reasons mentioned, it would be very desirable to have a process in which the alkyllithium compound to be used for the deprotonation is produced from the cheap raw materials haloalkane and lithium metal in an ether and is simultaneously or subsequently reacted with the substrate to be deprotonated, since this procedure would enable all the above-mentioned disadvantages of the "classical" production of lithium aromatics to be circumvented.

The present invention achieves all these objects and provides a process for preparing aryllithium compounds of the formulae (IV) and (VI) and also, if desired, reacting these compounds further with suitable electrophiles, in which a lithium compound (II) is firstly generated by reacting halogen compounds (I) with lithium metal and this is reacted with aromatic compounds of the formulae (III) and/or (V) with deprotonation and formation of the desired lithium aromatics (IV) and (VI) (equation I).

Step 1: Production of the Base

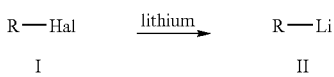

Step 2: Deprotonation of the substrate

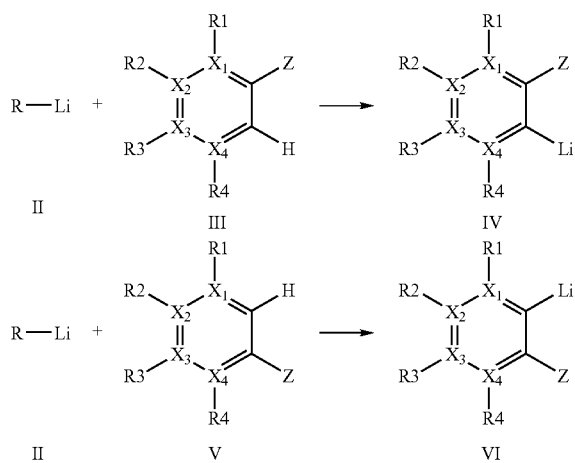

(Equation I)

where R is methyl, a primary, secondary or tertiary alkyl radical having from 2 to 12 carbon atoms, alkyl substituted by a radical from the group consisting of {phenyl, substituted phenyl, aryl, heteroaryl, alkoxy, dialkylamino, alkylthio} or substituted or unsubstituted cycloalkyl having from 3 to 8 carbon atoms, Hal=fluorine, chlorine, bromine or iodine, $X_{1-4}$ are, independently of one another, each carbon or the moiety $X_{1-4}R_{1-4}$ can be nitrogen or two adjacent radicals $X_{1-4}R_{1-4}$ can together be O (furans), S (thiophenes), NH or NR', where R' is $C_1$–$C_5$-alkyl, $SO_2$-phenyl, $SO_2$-p-tolyl or benzoyl.

Preferred compounds of the formula (III) which can be reacted by the process of the invention are, for example, benzenes, pyridines, pyridazines, pyrimidines, pyrazines, furans, thiophenes, N-substituted pyrroles, benzofurans, indoles or naphthalenes, to name only a few.

The radicals $R_{1-4}$ and the radical Z are substituents from the group consisting of {hydrogen, methyl, primary, secondary or tertiary, cyclic or acyclic alkyl radicals having from 2 to 12 carbon atoms, substituted cyclic or acyclic alkyl groups, alkoxy, dialkylamino, alkylamino, arylamino, diarylamino, phenyl, substituted phenyl, alkylthio, diarylphosphino, dialkylphosphino, dialkylaminocarbonyl or diarylaminocarbonyl, monoalkylaminocarbonyl or monoarylaminocarbonyl, $C_2^{31}$, hydroxyalkyl, alkoxyalkyl, fluorine and chlorine, CN and heteroaryl}, where in each case two adjacent radicals $R_{1-4}$ can together correspond to an aromatic or aliphatic ring.

The organolithium compounds prepared in this way can be reacted with any electrophilic compounds by-methods of the prior art. For example, C,C couplings can be carried out by reaction with carbon electrophiles, boronic acids can be prepared by reaction with boron compounds, and an efficient route to organosilanes is opened up by reaction with halosilanes or alkoxysilanes.

As haloaliphatics, it is possible to use all available or preparable fluoroaliphatics, chloroaliphatics, bromoaliphatics or iodoaliphatics, since lithium metal reacts easily and in virtually all cases in quantitative yields with all haloaliphatics in ether solvents. Preference is given to using chloroaliphatics or bromoaliphatics, since iodine compounds are often expensive and fluorine compounds lead to the formation of LiF which in later aqueous work-ups can form HF and lead to materials problems. However, such halides can also be used advantageously in specific cases.

In the process of the invention, preference is given to using alkyl halides which after the deprotonation can be converted into liquid alkanes.

Particular preference is given to using chlorocyclohexane or bromocyclohexane, benzyl chloride, tert-butyl chloride, chlorohexanes or chloroheptanes.

The reaction is carried out in a suitable organic solvent, with preference being given to ether solvents, for example tetrahydrofuran, dioxane, diethyl ether, di-n-butyl ether, diisopropyl ether or anisole. Preference is given to using THF.

Owing to the high reactivity of alkyllithium and aryllithium compounds, in particular toward, inter alia, the ethers used as solvents, the preferred reaction temperatures are in the range from −100 to +25° C., particularly preferably from −80 to −25° C.

A further advantage of the process of the invention is that it can be carried out at quite high concentrations of organolithium compounds. Preference is given to concentrations of the aliphatic or aromatic intermediates of the formula (II) of from 5 to 30% by weight, in particular from 12 to 25% by weight.

In the preferred embodiment, haloalkane and aromatic substrate are added simultaneously or as a mixture to lithium metal in ether. In this one-pot process (simultaneous addition of (I), (III) and/or (IV) to lithium in ether), the lithium aliphatic is formed first and this then immediately deprotonates the aromatic. In particular cases, especially when the aromatic can undergo secondary reactions with metallic lithium, it is possible firstly to produce the alkyllithium compound in ether by reaction of the haloaliphatic and lithium and only then introduce the aromatic substrate.

We have surprisingly found that in the preferred embodiment as a one-pot reaction, significantly higher yields are observed in virtually all cases compared to when RLi is generated first and the aromatic substrate is added only subsequently.

In the present process, the lithium can be used as dispersion, powder, turnings, sand, granules, lumps, bars or in another form, with the size of the lithium particles not being relevant to quality but merely influencing the reaction times. For this reason, relatively small particle sizes are preferred, for example granules, powders or dispersions. The amount of lithium added per mole of halogen to be reacted is from 1.95 to 2.5 mol, preferably from 1.98 to 2.15 mol.

In all cases, significant increases in the reaction rate can be observed when organic redox systems, for example biphenyl, 4,4-di-tert-butylbiphenyl or anthracene, are added in the reaction of the Li metal in the first stage. The addition of such systems has been found to be advantageous especially when the lithiation times are >12 hours without this catalysis.

Aromatics which can be used for the deprotonation are firstly all compounds which are sufficiently acidic to be able to be deprotonated under the conditions according to the invention. Here, mention may firstly be made of all aromatics having ortho-directing substituents Z, i.e. especially aromatics bearing alkoxy, F, Cl, substituted amino, CN, heteroaryl, aminoalkyl, hydroxyalkyl or similar radicals. The mode of action of such radicals is based on the fact that these substituents make coordination of the lithium ion of the aliphatic base possible, as a result of which the counterion R⁻ can then very easily deprotonate in the ortho position.

Furthermore, all heterocycles which are strongly acidic as the result of the combination of a plurality of effects, for example furan, may be mentioned here. The protons in this case are sufficiently acidic due to, inter alia, the inductive effect of the oxygen and due to the $sp^2$ hybridization and the angular stress on the α-carbon for deprotonation to be made possible. A similar situation applies in the case of other heterocycles.

In the other cases in which the aromatic protons to be replaced are not sufficiently acidic, the deprotonation can nevertheless be made possible by adding auxiliaries known to those skilled in the art for such problems. One auxiliary which has been found to be particularly useful for this purpose is potassium tert-butoxide which is added to the reaction mixture in amounts of from 0.05 to 1.2 equivalents during the lithiation of the haloaliphatic. In this way, even benzene, which has a low acidity, can be successfully lithiated (in some cases, such a procedure forms, partially or even entirely, the potassium aromatic, but since this has no effects on the nature of the reaction products formed, this aspect can be disregarded here).

The lithium aromatics generated according to the invention can be reacted with electrophilic compounds by the methods with which those skilled in the art are familiar, with carbon, boron and silicon electrophiles being of particular interest with a view to the intermediates required for the pharmaceutical and agrochemical industries.

The reaction with the electrophile can either be carried out after production of the lithiated compound (IV) and/or (VI) or, as described above, in a one-pot process by simultaneous addition to the reaction mixture.

The carbon electrophiles come, in particular, from one of the following categories (the products are in each case indicated in brackets):
aryl or alkyl cyanates (benzonitriles)
oxirane, substituted oxiranes (ArCH$_2$CH$_2$OH, ArCR$_2$CR$_2$OH) where R=R$^1$ (identical or different)
azomethines (ArCR$^1_2$—NR'H)
nitroenolates (oximes)
immonium salts (aromatic amines)
haloaromatic, aryl triflates, other arylsulfonates (biaryls)
carbon dioxide (ArCOOH)
carbon monoxide (Ar—CO—CO—Ar)
aldehydes, ketones (ArCHR$^1$—OH, ArCR$^1_2$—OH)
α,β-unsaturated aldehydes/ketones (ArCH(OH)-vinyl, CR$^1$(OH)-vinyl) ketenes (ArC(=O)CH$_3$ in the case of ketene, ArC(=O)—R$^1$ in the case of substituted ketenes)
alkali metal and alkaline earth metal salts of carboxylic acids (ArCHO in the case of formates, ArCOCH$_3$ in the case of acetates, ArR$^1$CO in the case of R$^1$COOMet)
aliphatic nitriles (ArCOCH$_3$ in the case of acetonitrile, ArR$^1$CO in the case of R$^1$CN)
aromatic nitriles (ArCOAr')
amides (ArCHO in the case of HCONR$_2$, ArC(=O)R in the case of RCONR'$_2$)
esters (Ar$_2$C(OH)R$^1$) or
alkylating agents (Ar-alkyl).

As boron electrophiles, use is made of compounds of the formula BW$_3$, where the radicals W are, independently of one another, identical or different and are each C$_1$–C$_6$-alkoxy, fluorine, chlorine, bromine, iodine, N(C$_1$–C$_6$-alkyl)$_2$ or S(C$_1$–C$_5$-alkyl), preferably trialkoxyboranes, BF$_3$*OR$_2$, BF$_3$*THF, BCl$_3$ or BBr$_3$, particularly preferably trialkoxyboranes.

As silicon electrophiles, use is made of compounds of the formula SiW$_4$, where the radicals W are, independently of one another, identical or different and are each C$_1$–C$_6$-alkoxy, fluorine, chlorine, bromine, iodine, N(C$_1$–C$_6$-alkyl)$_2$ or S(C$_1$–C$_5$-alkyl), preferably tetraalkoxysilanes, tetrachlorosilanes or substituted alkylhalosilanes or arylhalosilanes or substituted alkylalkoxysilanes or arylalkoxysilanes.

The process of the invention opens up a very economical method of bringing about the transformation of aromatic hydrogen into any radicals in a very economical way.

The work-ups are generally carried out in an aqueous medium, with either water or aqueous mineral acids being added or the reaction mixture being introduced into water or aqueous mineral acids. To achieve the best yields, the pH of the product to be isolated is set here, i.e. usually a slightly acidic pH and in the case of heterocycles also a slightly alkaline pH. The reaction products are, for example, isolated by extraction and evaporation of the organic phases; as an alternative, the solvents can also be distilled from the hydrolysis mixture and the product which then precipitates can be isolated by filtration.

The purities of the products from the process of the invention are generally high, but for special applications (pharmaceutical intermediates) it may nevertheless be necessary to carry out a further purification step, for example by recrystallization with addition of small amounts of activated carbon. The yields of the reaction products are in the range from 70 to 99%; typical yields are, in particular, from 85 to 95%.

The process of the invention is illustrated by the following examples, without being restricted thereto:

EXAMPLE 1

Preparation of 2,6-dimethoxyphenylboronic acid from resorcinol dimethyl ether and chlorocyclohexane A mixture of 20.88 g of chlorocyclohexane (0.176 mol) and 22.1 g of resorcinol dimethyl ether (0.16 mol) is added dropwise to a suspension of 2.35 g of lithium granules (0.34 mol) in 300 g of THF at −50° C., with an addition time of 2 hours being selected. After a conversion of the chlorocyclohexane of >97% determined by GC (total of 9 h), 16.6 g of trimethyl borate (0.16 mol) are added dropwise at the same temperature over a period of 15 minutes. After stirring for another 30 minutes at −50° C., the reaction mixture is poured into 120 g of water, the pH is adjusted to 6.3 by means of 37% HCl, and THF and cyclohexane are distilled off at 35° C. under reduced pressure. 25 ml of methylcyclohexane are added to the product suspension, the colorless product is filtered off with suction and is washed once with 25 ml of cold methylcyclohexane and once with 25 ml of cold water. After drying, 26.5 g of 2,6-dimethoxyphenylboronic acid (0.146 mol, 91%, melting point: 104–107° C.) are obtained in the form of colorless crystals, HPLC purity >99% a/a.

EXAMPLE 2

Preparation of 5-formylfuran-2-boronic acid from furfural diethyl acetal and chlorocyclohexane A mixture of 20.88 g of chlorocyclohexane (0.176 mol) and 27.2 g of furfural diethyl acetal (0.16 mol) is added dropwise to a suspension of 2.35 g of lithium granules (0.34 mol) in 300 g of THF at −65° C., with an addition time of 2 hours being selected. After a conversion of the chlorocyclohexane of >97% determined by GC (total of 10 h), 18.3 g of trimethyl borate (0.176 mol) are added dropwise at the same temperature over a period of 30 minutes. After stirring for another 30 minutes at −65° C., the reaction mixture is poured into 120 g of water, the pH is adjusted to 6.3 by means of 37% HCl, and THF and cyclohexane are distilled off at a maximum of 35° C. under reduced pressure. The pH is subsequently adjusted to 1.5, the mixture is stirred until all the product has precipitated and the product is filtered off. After washing with a little cold water and a little cold acetone and drying, 17.2 g of 5-formyl-2-furanboronic acid (0.123 mol, 77%) are obtained in the form of a fine beige powders, HPLC purity >99% a/a.

EXAMPLE 3

Preparation of the methyl ether of salicylic acid from anisole and chlorocyclohexane A mixture of 20.88 g of chlorocyclohexane (0.176 mol) and 17.3 g of anisole (0.16 mol) is added dropwise to a suspension of 2.35 g of lithium granules (0.34 mol) in 300 g of THF at −50° C., with an addition time of 2 hours being selected once again. After a conversion of the chlorocyclohexane of >97% determined by GC (total of 11 h) dry carbon dioxide is passed in at the same temperature until the solution is saturated with $CO_2$. After stirring for another 30 minutes at −50° C., the reaction mixture is poured into 100 g of water, the pH is adjusted to 3.4 by means of 37% HCl and the solvent is distilled off at a maximum of 55° C. under reduced pressure. The colorless product is filtered off with suction and, after drying, the methyl ether of salicylic acid (yield: 79%) is obtained in the form of colorless crystals, HPLC purity >99% a/a. A further amount of the methyl ether of salicylic acid can be obtained by extraction of the mother liquor with dichloromethane, drying over sodium sulfate and evaporation, total yield: 93%.

EXAMPLE 4

Preparation of 2,6-difluoroacetophenone from 1,3-difluorobenzene and acetic anhydride A solution of tert-butyllithium in THF is firstly produced by reacting 9.25 g of tert-butyl chloride with 1.4 g of lithium granules in 100 g of THF at −78° C. After a conversion of >97% (GC a/a) has been reached, 1,3-difluorobenzene (11.4 g) is added and the mixture is stirred for another 30 minutes at −78° C. and subsequently for 2 hours at −65° C. The resulting solution of 2,6-difluoro-1-lithiobenzene is added dropwise to a solution of 22 g of acetic anhydride in 35 g of THF which has been cooled to −5° C. After the usual aqueous work-up, 2,6-difluoroacetophenone is obtained in a yield of 92%.

EXAMPLE 5

Preparation of 2-(thienyl)ethanol from thiophene and 1-chloroheptane

A mixture of 145 g of 1-chloroheptane (1.1 mol) and 84.0 g of thiophene (1.0 mol) is added dropwise to a suspension of 14.5 g of lithium granules (2.1 mol) in 500 g of THF at −50° C. over a period of 3 hours. After a conversion of the chloroheptane of >97% determined by means of GC (total of 9 h), 48 g of ethylene oxide (1.1 mol) are passed in at the same temperature. After stirring for another 30 minutes at −50° C., the reaction mixture is poured into 120 g of water, the pH is adjusted to 5.9 by means of 37% HCl and the low boilers are distilled off at a maximum of 55° C. under reduced pressure. After extraction with 3×175 g of dichloromethane, drying over sodium sulfate, filtering off the desiccant and evaporation to dryness, thienylethanol is obtained in a yield of 83%.

EXAMPLE 6

Preparation of benzoic acid from benzene and chlorocyclohexane (deprotonation of benzene)

A mixture of 0.2 mol of chlorocyclohexane and 0.2 mol of benzene is added dropwise to a suspension of 0.4 mol of lithium granules, 0.21 mol of potassium tert-butoxide and 35 mg of biphenyl in 300 g of THF at −72° C. After a conversion of the chlorocyclohexane of >97% determined by means of GC (total of 24 h), carbon dioxide is passed in until saturation is achieved. The work-up is carried out by a method analogous to that in example 3; benzoic acid is obtained in a yield of 79%.

The invention claimed is:
1. A process for preparing aryllithium compounds of the formulae (IV) and (VI) comprising the steps of
   a. reacting at least one halogen compound (I) with lithium metal to form a lithium compound of the formula (II)

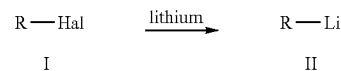

b. reacting the lithium compound of formula (II) with aromatic compounds of the formulae (III) and/or (V) to deprotonate the aromatic compounds of formulae (III) and/or (V) and form lithium aromatics of formulae (IV) and/or (VI), wherein the steps a) and b) are carried out as a one-pot reaction,

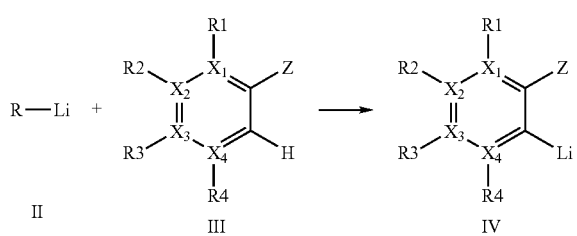

-continued

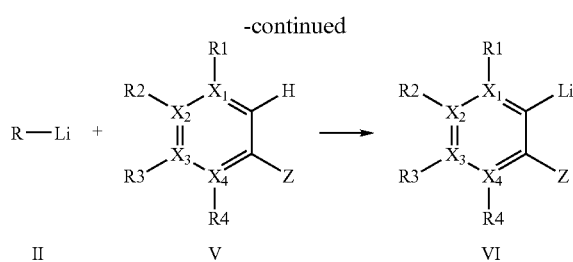

II    V    VI where R is methyl, a primary, secondary or tertiary alkyl radical having from 2 to 12 carbon atoms, alkyl substituted by a radical selected from the group consisting of phenyl, substituted phenyl, aryl, heteroaryl, alkoxy, dialkylamino, alkylthio and substituted or unsubstituted cycloalkyl having from 3 to 8 carbon atoms, Hal=fluorine, chlorine, bromine or iodine, $X_{1-4}$ are, independently of one another, each carbon or two adjacent radicals $X_{1-4}R_{1-4}$ can together be O, or S;

the radicals $R_{1-4}$ and the radical Z are substituents selected from the group consisting of hydrogen, methyl, primary, secondary or tertiary, cyclic or acyclic alkyl radicals having from 2 to 12 carbon atoms, substituted cyclic or acyclic alkyl groups, alkoxy, dialkylamino, alkylamino, arylamino, diarylamino, phenyl, substituted phenyl, alkylthio, diarylphosphino, dialkylphosphino, dialkylaminocarbonyl or diarylaminocarbonyl, monoalkylaminocarbonyl or monoarylaminocarbonyl, $CO_2^-$, hydroxyalkyl, alkoxyalkyl, fluorine and chlorine, CN and heteroaryl or two adyacent radicals $R_{1-4}$ form an aromatic or aliphatic ring.

2. The process as claimed in claim 1, wherein the process is carried out at temperatures in the range from −100 to +25° C.

3. The process as claimed in claim 1, wherein the amount of lithium to be added per mole of halogen to be reacted is in the range from 1.95 to 2.5 mol.

4. The process as claimed claim 1, wherein the process is carried out in an ether solvent.

5. The process as claimed in claim 1, said process further comprising adding organic redox systems to the reaction of the Li metal in step a).

6. The process as claimed in claim 1, wherein the compounds of the formula (III) or (V) include an alkoxy, F, Cl, substituted amino, CN, heteroaryl, aminoalkyl or hydroxyalkyl radical in the ortho position relative to the deprotonating hydrogen.

7. The process as claimed in claim 1, further comprising the step of reacting the compounds of the formulae (IV) and/or (VI) with an electrophile.

8. The process as claimed in claim 7, wherein the reaction with the electrophile is carried out either after production of the lithiated compound (IV) and/or (V) or in a one-pot process by simultaneous addition to the reaction mixture.

9. The process as claimed in claim 7, wherein the electrophile is selected from the group consisting of carbon, boron or silicon compounds.

10. The process as claimed in claim 1, wherein two adjacent radicals $R_{1-4}$ form an aromatic or aliphatic ring.

11. A process as claimed in claim 1, wherein the lithium compound of the formula (II) is present in a concentration ranging from 5 to 30% by weight.

12. A process for preparing aryllithium compounds of the formula (IV) and (VI) comprising the steps of
a. reacting at least one halogen compound (I) with lithium metal to form a lithium compound of the formula (II)

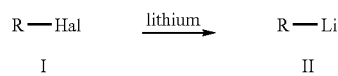

b. reacting the lithium compound of formula (II) with aromatic compounds of the formula (III) and/or (V) to deprotonate the aromatic compounds of formula (III) and/or (V) and form lithium aromatics of formula (IV) and/or (VI).

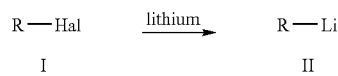

where R is methyl, a primary, secondary or tertiary alkyl radical having from 2 to 12 carbon atoms, alkyl substituted by a radical selected from the group consisting of phenyl, substituted phenyl, aryl, heteroaryl, alkoxy, dialkylamino, alkylthio and substituted or unsubstituted cycloakyl having from 3 to 8 carbon atoms, Hal=fluorine, chlorine, bromine or iodine, $X_{1-4}$ are, independently of one another, each carbon or two adjacent radicals $X_{1-4}R_{1-4}$ can together be O, or S;

the radicals $R_{1-4}$ and the radical Z are substituents selected from the group consisting of hydrogen, methyl, primary, secondary or tertiary, cyclic or acyclic alkyl radicals having from 2 to 12 carbon atoms, substituted cyclic or acyclic alkyl groups, alkoxy, dialkylamino, alkylamino, arylamino, diarylamino, phenyl, substituted phenyl, alkylthio, diarylphosphino, dialkylphosphino, dialkylaminocarbonyl or diarylaminocarbonyl, monoalkylaminocarbonyl or monoarylaminocarbonyl, $CO_2^-$, hydroxyalkyl, alkoxyalkyl, fluorine and chlorine, CN and heteroaryl, or two adjacent radicals $R_{1-4}$ form an aromatic or aliphatic ring, wherein (I) the process is carried out at temperatures in the range from −100 to −25° C. and (II) the process is carried out in an ether solvent.

* * * * *

UNITED STATES PATENT AND TRADEMARK OFFICE
CERTIFICATE OF CORRECTION

PATENT NO. : 7,208,614 B2
APPLICATION NO. : 10/491966
DATED : April 24, 2007
INVENTOR(S) : Meudt Page 1 of 1

It is certified that error appears in the above-identified patent and that said Letters Patent is hereby corrected as shown below:

Column 9,
Claim 1, Line 30, delete "dialkyiphos-" insert --dialkylphos --
Claim 1, Line 34, delete "adyacent" insert -- adjacent--

Claim 12, Line 25, delete " 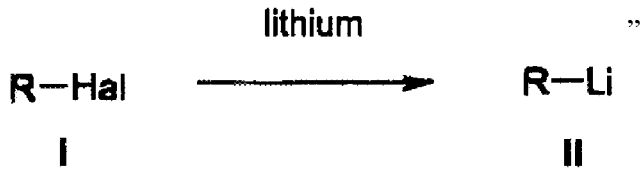 "

insert --

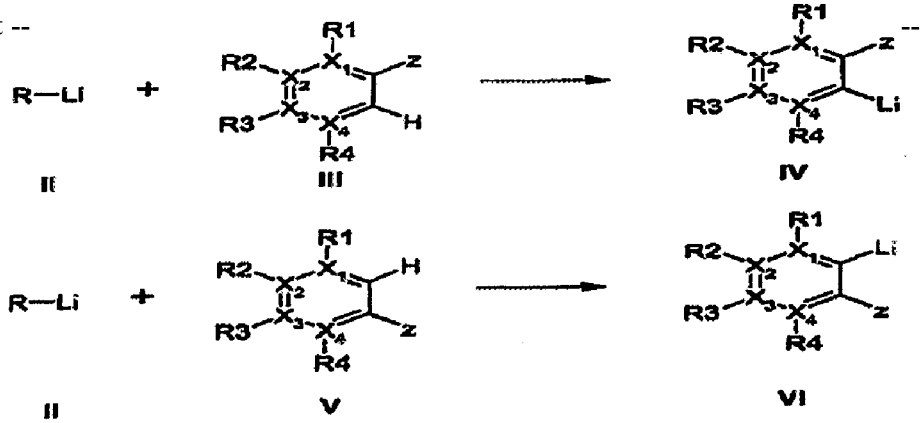

Claim 12, Line 37, delete "cycloakyl" insert --cycloalkyl--

Signed and Sealed this

Nineteenth Day of June, 2007

JON W. DUDAS
*Director of the United States Patent and Trademark Office*